(12) United States Patent
Lin et al.

(10) Patent No.: US 10,028,720 B2
(45) Date of Patent: Jul. 24, 2018

(54) QUALITY CONTROL PHANTOM

(71) Applicant: Carestream Health, Inc., Rochester, NY (US)

(72) Inventors: Yuan Lin, Rochester, NY (US); William J. Sehnert, Fairport, NY (US); Karin Toepfer, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 33 days.

(21) Appl. No.: 14/876,120

(22) Filed: Oct. 6, 2015

(65) Prior Publication Data

US 2016/0095569 A1    Apr. 7, 2016

Related U.S. Application Data

(60) Provisional application No. 62/060,602, filed on Oct. 7, 2014.

(51) Int. Cl.
*A61B 6/00* (2006.01)
*A61B 6/03* (2006.01)

(52) U.S. Cl.
CPC .............. *A61B 6/583* (2013.01); *A61B 6/032* (2013.01); *A61B 6/4085* (2013.01)

(58) Field of Classification Search
CPC ...................................................... A61B 6/593
See application file for complete search history.

(56) References Cited

U.S. PATENT DOCUMENTS

| 7,339,159 B2* | 3/2008 | Juh ......................... A61B 6/12 |
| | | 250/252.1 |
| 9,681,851 B2* | 6/2017 | Rohler ................... A61B 6/583 |
| 2008/0095302 A1 | 4/2008 | Ruhrnschopf et al. |
| 2010/0167251 A1* | 7/2010 | Boutchko .............. A61B 5/416 |
| | | 434/267 |

FOREIGN PATENT DOCUMENTS

WO    2016/003957 A2    1/2016

\* cited by examiner

*Primary Examiner* — Dani Fox

(57) ABSTRACT

A quality control phantom comprises a container and a frame to secure quality control accessories in position within the container during radiologic exposure testing.

20 Claims, 2 Drawing Sheets

QUALITY CONTROL PHANTOM

CROSS REFERENCE TO RELATED APPLICATIONS

This application claims the benefit of U.S. Provisional application U.S. Ser. No. 62/060,602, provisionally filed on Oct. 7, 2014, entitled "QUALITY CONTROL PHANTOM FOR CBCT", in the names of Yuan Lin et al., which is incorporated herein by reference in its entirety.

BACKGROUND OF THE INVENTION

The present invention relates generally to x-ray computed tomography (CT) imaging and, more particularly, to a phantom for CT and cone beam CT (CBCT) image quality testing and quality control purposes.

Imaging phantoms may comprise specially designed objects that may be exposed to radiographic energy in an imaging system. Because the phantoms comprise known materials, material properties, and shapes, a phantom may be used to evaluate an imaging device, such as a CT or a CBCT imaging system, by comparing captured images of the phantom with the phantom itself or with expected results. Other performance parameters of the imaging system may also be evaluated by using phantoms in this way. For instance, phantoms may comprise known quantities and arrangements of contrast agents which may or may not be similar to human or other mammalian body tissues. Similarly, phantoms may be designed to simulate materials common in industrial applications that are tested by using x-rays. Thus, absorption and scattering properties of an x-ray imaging system used in a variety of applications may be tested.

The discussion above is merely provided for general background information and is not intended to be used as an aid in determining the scope of the claimed subject matter.

BRIEF DESCRIPTION OF THE INVENTION

A quality control (QC) phantom comprises a housing in the form of a container that holds a fill material and a frame. Objects of various shapes are removably secured in position within the container during radiologic exposure testing. An advantage that may be realized in the practice of some disclosed embodiments of the QC phantom may be easier, faster, and less expensive testing set-up for radiological imaging equipment.

In one embodiment, a method of making and using a quality control phantom is disclosed wherein a container is provided, a fill material is used to at least partially fill the container, and one or more quality control accessories are fixed in position within the container.

In another embodiment, a phantom apparatus comprises a container, a fill material within the container, and a frame within the container having objects attached thereto. The frame secures the objects in a fixed position within the container.

So that the manner in which the features of the invention can be understood, a detailed description of the invention may be had by reference to certain embodiments, some of which are illustrated in the accompanying drawing. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawing below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate a like part or parts. Thus, for further understanding of the invention, reference can be made to the following detailed description, read in connection with the drawings in which.

DETAILED DESCRIPTION OF THE INVENTION

Figure 1:
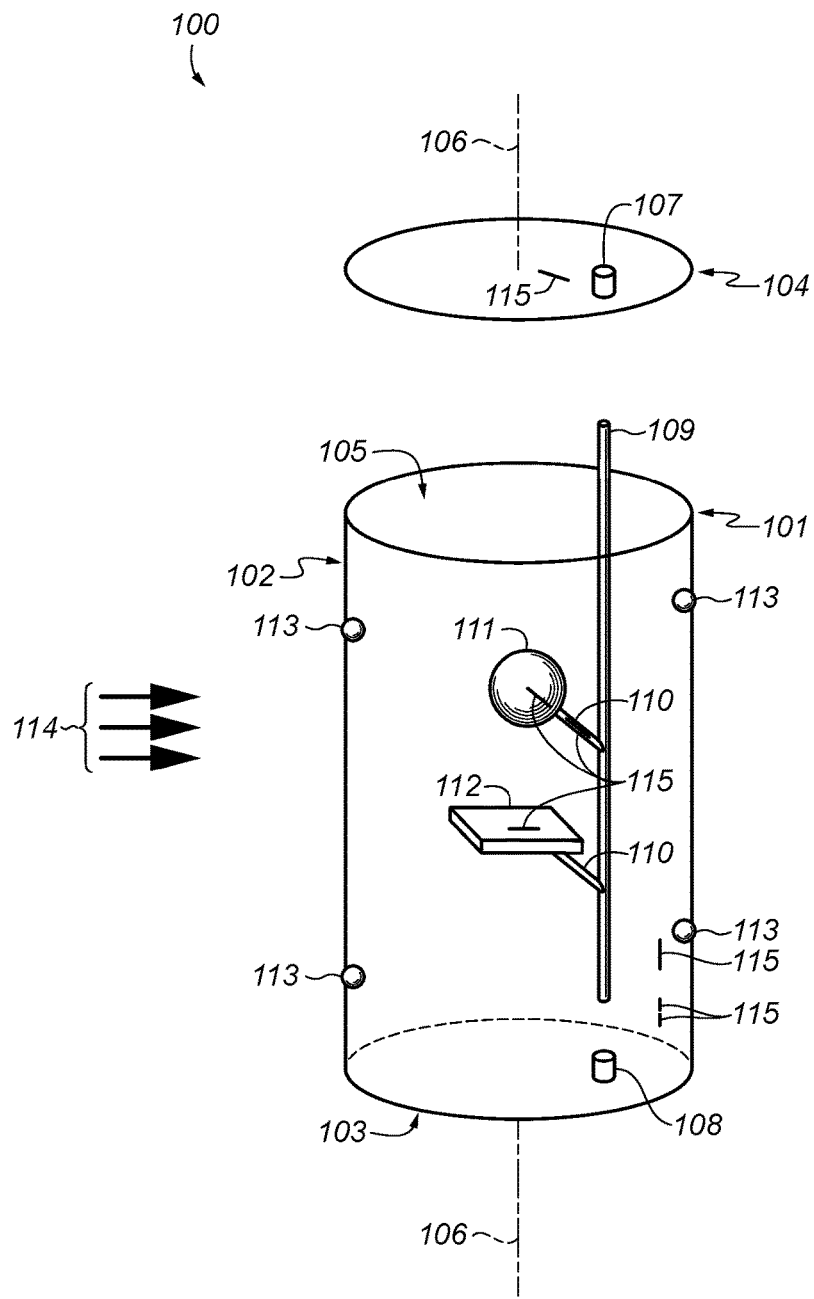
FIG. 1 is a perspective transparent view of an exemplary phantom apparatus embodiment disclosed herein.

FIG. 1 shows an exemplary phantom apparatus 100 having a container 101 shaped in the form of a cylinder 102 with a closed bottom surface 103. In one embodiment, the bottom surface 103 may be attached to the cylinder 102 in a fluid tight fashion. In another embodiment, the container 101 and the bottom surface 103 may be fabricated integrally, such as fabricating a can with an open top. A lid 104 for the open end 105 of the container 101 may be configured to be manually or mechanically attachable to the container 101 to cover the open end 105. In one embodiment, the lid 104 is attachable in a fluid tight fashion. The lid 104 may be attachable to the container 101 via a compression fit, snaps, threads, or other suitable means. In one embodiment, the lid 104 may be loosely placed on top of the container 101 over the open end 105. The cylinder 102 may be said to define a central axis 106. In one embodiment, the container 101, bottom surface 103, and lid 104, are made from the same or similar material which is sufficiently rigid to perform imaging phantom functions as described herein. Although, the container 101 has been shown and described in the shape of a cylinder, the container 101 may be fabricated to resemble a conical, frustoconical, cubic, rectangular, regular or irregular (asymmetrical) polyhedral, or ellipsoid shape. The container 101 may be made from polyvinyl chloride (PVC), polymethyl methacrylate (PMMA), Teflon, polystyrene, carbon, or plastic, or a combination thereof. In one embodiment, the container 101 may be made from a radiolucent material. In one embodiment, the lid 104 and the bottom surface 103 are made from the same or different radiolucent material as the container 101, or they may be made from a different radiopaque material.

A feature, such as a notch 107, may be formed in the lid 104, and a matching feature, such as a notch 108, may be formed in the bottom surface 103. Such a notch 107, 108, may be etched or indented in the lid 104 or the bottom surface 103, or formed using other suitable methods. Such a feature may also be formed by affixing a notch piece to the lid 104 or the bottom surface 103. The notches 107, 108, (or notch pieces) may be used as positioning features to secure a rod 109 in a desired location within the container 101. The notches 107, 108, and the rod 109 may be configured so that ends of the rod 109 may each be manually positioned in one of the notches, such as by inserting the ends of the rod 109 into the notches 107, 108. Because the lid 104 may be fixedly attached to the container 101, the rod 109 may be fixed in the desired position within the container 101. In one embodiment, the notch 108 in the bottom surface 103 of the container 101 is configured to securely hold the rod 109 in position without requiring an opposite end of the rod 109 to be inserted in the notch 107 in the lid 104. In one embodiment, the notch 107 in the lid 104 is configured to securely hold the rod 109 in position without requiring an opposite end of the rod 109 to be inserted in the notch 109 in the bottom surface 103. Ends of the rod 109 may be configured to be compression fitted in the notches 107, 108, or they may be threaded, or otherwise include suitable means for attachment within the container 101. In one embodiment, the notches 107, 108, and the rod 109, are configured so that the rod 109 is positioned substantially parallel to the central axis 106 of the container 101.

A plurality of arms 110 may be connected to, and extend away from, the rod 109 whereby each of the arms 110 have affixed thereto a QC accessory. The rod 109 and the arms 110 as a functional unit may be referred to herein as a frame. A first exemplary QC accessory may be shaped as a sphere 111, and a second exemplary QC accessory may be shaped as a square plane, or plate, 112, although various other shapes may be used. In one embodiment, the QC accessories secured within the container 101 are selected to have shapes having at least one axis of symmetry. The arms 110 may be manually attached to, and detached from, the rod 109 by drilling holes in the rod 109 whereby the arms 110 may be inserted therein, by a compression fit or threaded, for example, or otherwise securably attached to the arm for positioning various QC accessories independently in various combinations and at different heights and orientations. Similarly, the QC accessories may be configured to be manually attachable to and detachable from any of the arms 110 in a likewise fashion. In one embodiment, the arrangement of QC accessories within the container 101 may be oriented along the central axis 106 so that x-rays 114 propagate in a direction generally perpendicular to the central axis 106 to pass through the side of the cylinder 102.

Other exemplary QC accessories may be positioned within the container 101 as desired, such as exemplary QC accessories shaped as spherical beads 113 which may be attached to, or embedded in, an inside surface of the container 101. In one embodiment, the phantom apparatus 100 comprises beads 113 embedded in the container 101 material without utilizing a frame 109, 110. The QC accessories described herein, as well as the frame 109, 110, may be shaped in any form and may be made from any desired materials, such as PVC, PMMA, a metal such as titanium, or Teflon. Exemplary QC accessories may be solid or hollow and have shapes including cylindrical, conical, frustoconical, cubic, rectangular, cross-shaped, plate, disk, spherical, and other regular or irregular (asymmetric) polyhedral and ellipsoid shapes. The QC accessories may be objects made from homogeneous solids or non-homogeneous solids, and may be fluid filled objects. In one embodiment, the QC accessories are selected so that they include a smooth defect-free construction and do not exhibit fabrication artifacts such as welding seams. In one embodiment, the container 101, the QC accessories, and the frame 109, 110, comprise only rounded edges and no seams in the material from which they are made.

In one embodiment, the phantom apparatus 100 encloses an interior volume having a plurality of QC accessories secured therein to be used for testing various image quality metrics of a radiographic imaging system, such as a CT or CBCT imaging system. The image quality metrics may include an imaging system's modulation transfer function (MTF), contrast scale, or other system parameters such as spectral parameters or geometric calibration. Other phantoms such as in the form of material slabs may be placed in the container 101 for QC testing, including wedge phantoms, stepped phantoms, and the like.

The plurality of QC accessory objects may be selected based on material or shape for different image quality quantification purposes. For example, a cross-shaped QC accessory may be used to test the accuracy of a patient alignment system, for example, a laser system or optical system. Edge phantoms, such as a plate, disk, cube, cylinder, or sphere, wire phantoms, and bead phantoms may be used for MTF measurements. Various shapes of metal QC accessories may be used for metal artifacts assessment.

A PMMA or polystyrene plate, disk, cube, cylinder, sphere, etc., may be used to quantify the CT number of PMMA or polystyrene, or its contrast scale. A QC accessory shaped as a plate with multiple inserts made of different materials, e.g., PVC, Teflon, PMMA, polystyrene, air, etc., may be used to quantify the Hounsfield unit linearity. A bone mineral density (BMD) plate having different BMD inserts may be used to calibrate bone density curves. A low contrast spatial resolution plate with different sizes of holes may be used to test the low contrast properties of a CT or CBCT imaging system. The dimensions of the inserts may be used as geometric accuracy assessment tools.

In one embodiment, the container 101 may be partially or completely filled with liquid, such as water, so as to be used as a water phantom to measure, for example, a CT number associated with the water phantom, or the noise of water, image uniformity, artifacts, and the like. In one embodiment, the frame 109, 110, may be made of water-equivalent material and may be inserted into the water-filled container 101 and fixed in position using the positioning notches 107, 108, as described herein. Although the container 101 has been described herein as being filled with a liquid such as water, the container 101 may remain unfilled, or it may be filled with another fill material such as gel, plasma, oil, another liquid, fluid, or semi-solid material, or a combination thereof. The selected fill material may be used to secure in position one or more QC accessories within the container 101 without using a frame 109, 110.

In one embodiment, the container 101, the frame 109, 110, and the QC accessories may include visible alignment markings 115 drawn, etched, or otherwise formed, thereon. Alignment markings 115 on the frame 109, 110, may be used to align the frame 109, 110, with alignment markings 115 on the inside surface or outside surface of the container 101. Alignment markings 115 on the QC accessories may be used to align the QC accessories with alignment markings 115 on the arms 110. Alignment markings 115 on the outside surface of the container 101 or lid 104 may be used to indicate locations of the frame 109, 110, or QC accessories within the container 101 when the lid 104 is secured over the open end 105 of the container 101.

Multiple QC accessories with or without inserts may be used at the same time. The water phantom and the QC accessories may be designed into various sizes according to the purposes the radiological scan test or exposure test. Embodiments of the phantom apparatus 100 described herein may be modified to include materials now known or discovered in the future and are considered within the scope of the claims.

Figure 2A:
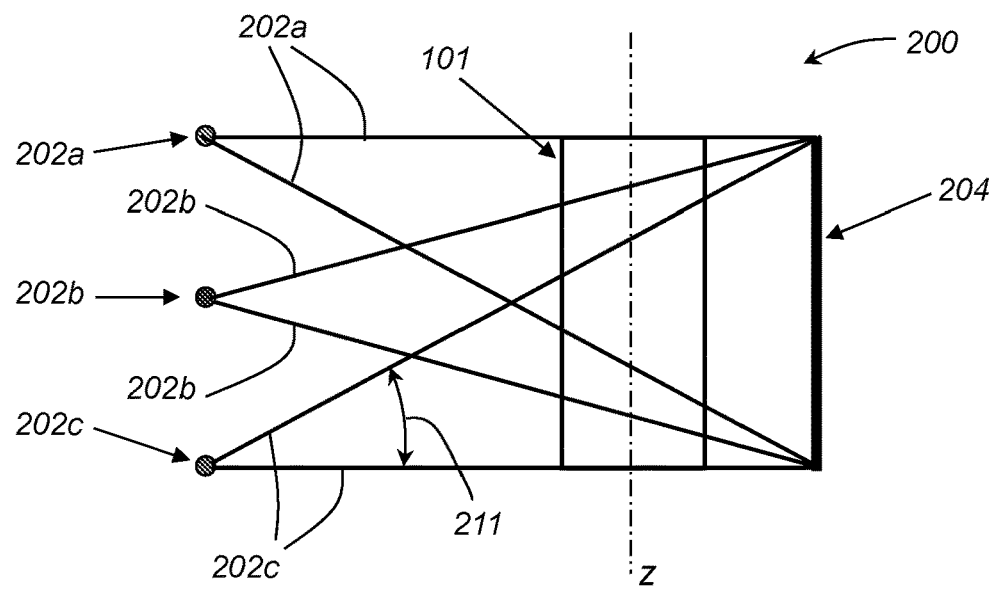
FIGS. 2A-2B are schematic diagrams of an exemplary single and multi-source CBCT imaging system using the phantom apparatus of FIG. 1.
Figure 2B:
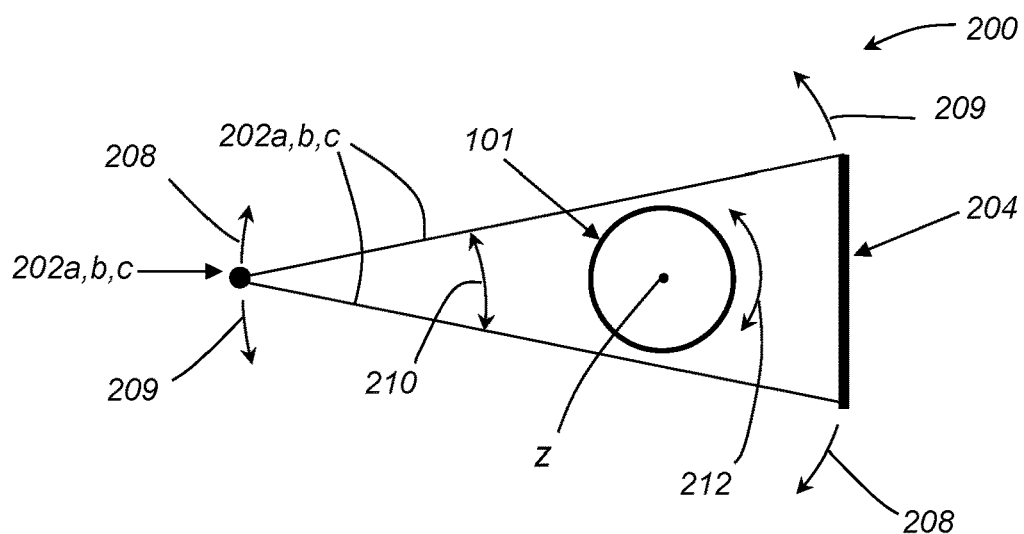

FIGS. 2A-2B illustrate a schematic diagram of an imaging system 200 comprising one or more radiographic energy (x-ray) sources 202a-c aimed at a phantom apparatus 101 to be imaged for purposes of testing the imaging system 200. A digital radiographic (DR) detector 204 is positioned in a known and predetermined geometric relationship with the x-ray sources 202a-c wherein the phantom apparatus 101 to be imaged is positioned therebetween. The structural details of the phantom apparatus 101 are explained herein and are not shown in the FIGS. 2A-2B for purposes of clarity in the figures. In one embodiment, the x-ray sources 202a-c and the DR detector 204 may form a portion of a CBCT imaging system 200, whereby one or more of the x-ray sources 202a-c and the detector 204 are configured to revolve about an imaging axis z while capturing a plurality of digital projection (2D) images of the phantom apparatus 101 in the detector 204, as is well known in the digital radiography arts. The captured images may be processed in, or transmitted by, the detector 204. If transmitted, the detector may use wired or wireless transmission to an attached computer system for processing, such as for reconstructing a 3D image from the captured projection images.

In one embodiment, the phantom apparatus to be imaged 101 is positioned so as to coincide with the imaging axis z, although such positioning is not required, and adequate images of the phantom apparatus 101 may be captured and/or reconstructed by the system 200 if the phantom apparatus 101 is positioned proximate to the imaging axis z. The one or more x-ray sources 202a-c may each be configured to controllably emit, or fire, an x-ray beam 202a-c, respectively, such as a cone beam, aimed at phantom apparatus 101 and toward the DR detector 204. The shapes of the x-ray beams 202a-c are not intended to illustrate a limiting shape of the x-ray beams 202a-c. FIG. 2B is a schematic top view of the imaging system 200 illustrating an exemplary embodiment of the imaging system 200 whereby the x-ray sources 202a-c are arranged collinearly in a line parallel to the imaging axis z.

In one embodiment, to complete a CBCT scan of the phantom apparatus 101, at least one of the sources 202a-c are selectively and controllably fired multiple times while simultaneously revolving both the selected one or more of sources 202a-c and the detector 204 about axis z for at least a portion of one revolution thereabout, i.e., 360° or less, in either of the directions indicated by arrows 208 or 209, while maintaining the selected one or more sources 202a-c and detector 204 diametrically opposed in relation to the axis z. Alternatively, and equally effective, the selected one or more of sources 202a-c and the detector 204 may be fixed in position without movement while the phantom apparatus 101 is rotated about the axis z in either of the directions indicated by the arrow 212. Each firing of the selected one or more of the sources 202a-c generates a different radiographic projection image (2D) of the phantom apparatus 101, depending on its angular position, that is digitally captured by detector 204. In one embodiment, the selected one or more of the sources 202-a-c is fired multiple times at angular points equidistant from each other as it revolves about axis z for one complete revolution. Similarly, the selected one or more of the sources 202-a-c may be fired multiple times while the phantom apparatus 101 is rotated at angular positions that are equidistant from each other for one complete revolution. In one embodiment, the selected one or more of the sources 202a-c is fired 360 times during one revolution (360° scan) or rotation about axis z, each firing occurring substantially one degree apart. In another embodiment, the selected one or more of the sources 202a-c is each fired 3600 times during one revolution or rotation about axis z, each firing also occurring at angular points substantially equidistant from each other. It will be recognized by persons skilled in the art that any number of images may be captured during one revolution of a selected one or more of the sources 202a-c and detector 204, limited only by the mechanical and electrical characteristics of the imaging system 200. It will be appreciated by one skilled in the art that x-rays may be emitted from the one or more sources 202a-c with a representative predetermined cone beam angle 210, 211. In one embodiment, during the digital image data acquisition procedure, which may be referred to herein as an imaging scan, a 360 scan, or a scanning sequence, for example, the one or more sources 202a-c revolve over a predetermined circular trajectory in relation to the phantom apparatus 101 in unison with the detector 204 such that the detector 204 acquires circular cone beam image data.

It is well known that imaging system 200 as depicted in FIGS. 2A-B may include only one or only two of the x-ray sources 202a-c . Thus, the embodiments disclosed herein are not limited only to using three x-ray sources 202a-c in imaging system 200 and are equally applicable to imaging systems using only one, or only two, of the x-ray sources 202a-c . An exemplary CBCT imaging system, that may be applicable for use of the phantom apparatus 101, is described in commonly owned U.S. Pat. No. 8,348,506, issued Jan. 8, 2013, and entitled Extremity Imaging Apparatus for Cone Beam Computed Tomography, which is hereby incorporated by reference as if fully set forth herein in its entirety.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A phantom apparatus comprising:
a fluid tight container comprising horizontal top and bottom surfaces and one or more vertical sidewalls extending between the top and bottom surfaces;
a fill material within the container;
a frame extending between the top and bottom surfaces within the container;
a plurality of arms each having one end attached to the frame at predetermined different locations along a length of the frame, each of the arms extending away from the frame; and
a plurality of separate objects each attached to one arm at an end of the one arm extended away from the frame, wherein the frame is configured to secure in a fixed position each of the plurality of separate objects within the container.

2. The apparatus of claim 1, wherein the frame is configured to attach to each of the top and bottom surfaces.

3. The apparatus of claim 2, wherein the one or more sidewalls define a central axis of the container, and wherein the frame comprises a rod extending along a line substantially parallel with the central axis of the container.

4. The apparatus of claim 3, wherein the fill material comprises water.

5. The apparatus of claim 4, wherein the plurality of separate objects include a solid sphere and a plate.

6. The apparatus of claim 5, wherein the top surface and the frame are configured to be manually removable from the container and replaceable on or in the container.

7. The apparatus of claim 6, wherein the objects are configured to be detachable and reattachable to the rod.

8. The apparatus of claim 1, wherein one of the top and bottom surfaces comprises an attachment feature for securing the frame thereto.

9. The apparatus of claim 1, wherein the one or more sidewalls comprise a plurality of metal beads embedded therein.

10. The apparatus of claim 1, wherein the objects and the container each comprise a shape selected from the group consisting of cylindrical, conical, frustoconical, cubic, and rectangular shapes, regular and irregular rounded polyhedra and ellipsoids.

11. The apparatus of claim 10, wherein the objects, the frame and the container are each made from a material selected from the group consisting of PVC, Teflon, PMMA, polystyrene, titanium, other metals, and plastics.

12. The apparatus of claim 1, further comprising one or more selected materials different from a material of the container, embedded in or attached to the container to be used for geometric calibration of an imaging system using x-rays.

13. The apparatus of claim 1, further comprising one or more visible alignment markings on an exterior surface of the container, each of the alignment markings aligned with a position of the frame within the container, a position of one of the separate objects within the container, or a combination thereof.

14. A phantom apparatus comprising:
a rigid cylindrical container having parallel top and bottom surfaces;
a fill material within the container;
a rigid frame within the container that attaches to the top and bottom surfaces to secure the rigid frame in a fixed position; and
a plurality of separate objects individually attached to the frame, wherein the frame secures in a fixed position the plurality of separate objects within the container.

15. The apparatus of claim 14, wherein the top surface is a removable surface to provide access into the container, the rigid frame comprises a rod, and wherein the plurality of objects are each shaped to have at least one axis of symmetry.

16. The apparatus of claim 14, wherein the plurality of objects include a solid sphere and a plate.

17. The apparatus of claim 14, wherein the container comprises a marking on an exterior surface thereof corresponding to a position of either the frame or one of the plurality of objects in the container.

18. The apparatus of claim 14, wherein the plurality of objects are attached to the frame at different heights within the container.

19. The apparatus of claim 14, further comprising a plurality of arms to attach the plurality of objects to the frame, wherein each arm comprises a first end attached to the frame and a second end attached to one object, and wherein the plurality of arms each extend from the frame in a different direction.

20. An apparatus comprising:
a rigid container having top and bottom surfaces, and sidewalls connected to the top and bottom surfaces; and
an interior of the container consisting of:
a fluid fill material;
a rigid frame fixed in a position extending between the top and bottom surfaces, wherein most of the frame is disposed within the fluid fill material;
a plurality of rigid arms each attached to the frame at different heights within the container; and
a plurality of separate objects each attached to one of the arms, wherein at least one of the objects is disposed in the fluid fill material,
wherein the separate objects are secured in a fixed position within the container, and wherein the objects are formed into preselected geometric shapes.

* * * * *